(12) United States Patent
Dominguez et al.

(10) Patent No.: US 8,763,615 B1
(45) Date of Patent: Jul. 1, 2014

(54) PORTABLE SONIC FLOSSER

(76) Inventors: Rebecca Dominguez, Sylmar, CA (US); Lisette Prellezo, San Fernando, CA (US)

( * ) Notice: Subject to any disclaimer, the term of this patent is extended or adjusted under 35 U.S.C. 154(b) by 121 days.

(21) Appl. No.: 13/603,858

(22) Filed: Sep. 5, 2012

(51) Int. Cl.
*A61C 15/00* (2006.01)

(52) U.S. Cl.
USPC ........................................... 132/322

(58) Field of Classification Search
USPC ................... 132/321–329; 15/167.1; 433/141
See application file for complete search history.

(56) References Cited

U.S. PATENT DOCUMENTS

| | | | |
|---|---|---|---|
| 4,605,025 A * | 8/1986 | McSpadden | 132/322 |
| 5,016,660 A | 5/1991 | Boggs | |
| 5,069,233 A | 12/1991 | Ritter | |
| 5,176,157 A * | 1/1993 | Mazza | 132/322 |
| 5,184,632 A * | 2/1993 | Gross et al. | 132/326 |
| 5,188,133 A | 2/1993 | Romanus | |
| 5,261,430 A | 11/1993 | Mochel | |
| 5,267,579 A | 12/1993 | Bushberger | |
| 5,343,883 A | 9/1994 | Murayama | |
| D493,577 S | 7/2004 | Winkler | |
| D503,496 S | 3/2005 | Nanda | |
| 6,886,570 B2 * | 5/2005 | Lai et al. | 132/309 |
| D526,091 S | 8/2006 | Winkler et al. | |
| 7,114,506 B2 | 10/2006 | Junkins | |

* cited by examiner

*Primary Examiner* — Robyn Doan

(57) ABSTRACT

A portable sonic flosser system to assist teeth cleaning, the system comprising a cylindrical handle, a hollow extension, a vibrator box, two arms disposed along the opposite sides of the vibrator. The handle has a floss roll, a timer, a microprocessor and battery disposed inside. A hollow extension extends from the handle with a cutter and two elongated hollow rubber guides disposed on opposite sides of extension exterior surface. A vibrator box is disposed at the top of the cone extension with two side arms to hold floss. A thread of floss is extracted from the floss roll inside the handle and fed through the first rubber guide, the first arm, the second arm and the second rubber guide, then tightened after closing the flanges on the distal end of both arms. After power on, the floss is vibrated supersonically by the vibrator to clean the teeth.

12 Claims, 3 Drawing Sheets

(Front View)

(Bottom View)

(Side View)

(Back View)

(Block Diagram)

PORTABLE SONIC FLOSSER

FIELD OF THE INVENTION

The present invention is directed to a powered flosser, more particularly to a portable power flosser with supersonic vibration frequency that can clean the teeth.

BACKGROUND OF THE INVENTION

Flossing is a common method besides tooth brushing for oral hygiene. Dental floss is made of thin nylon filaments or a plastic such as Teflon used to remove food residue and dental plaque from teeth. The floss is gently inserted between the teeth and scraped along the teeth sides, especially close to the gums. Dental floss is held between the fingers or strung on a fork like instrument. The floss is typically guided between each tooth manually to remove particles of food stuck between teeth and dento-bacterial plaque that adhere to such dental surfaces. Because of the thin thread, users may suffer finger pain or arm muscle fatigue over relative long time use. Moreover, the plastic floss fork are normally one-time usage and thus environmental unfriendly. Hence, there is a need for a need for a power flosser without replacing the floss-holding folk every time after usage.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a portable sonic flosser system to assist teeth cleaning. The system comprising a cylindrical handle, a hollow extension, a vibrator box, two arms disposed along the opposite sides of the vibrator. The handle has a floss roll, a timer, a microprocessor and battery disposed inside. A hollow extension with an oblique circular truncated cone shape extends from the handle. The extension has a first and second elongated hollow rubber guides disposed on the opposite sides of the said cone exterior surface and a cutter disposed on the exterior of the extension base. A vibrator box is disposed at the top of the cone extension with two side clip to hold floss. A thread of floss is extracted from the floss roll inside the said handle and pass through the first rubber guide, the first clip, the second clip, the second rubber guide and the cutter, then tightened via the clips when the clip button pressed to close the clips. After power on, the floss is vibrated supersonically together with the arms by the vibrator to clean the teeth.

DESCRIPTION OF PREFERRED EMBODIMENTS

Figure 1:
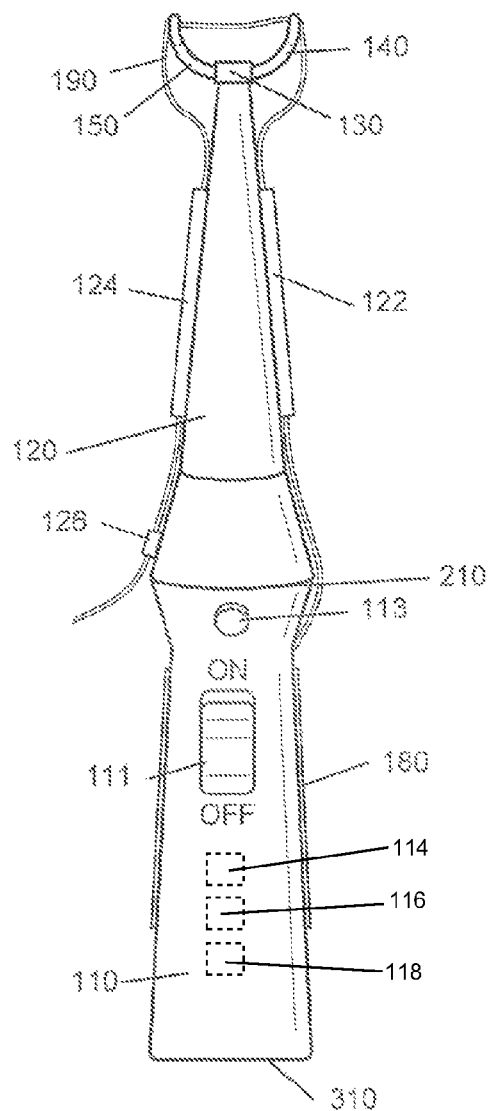
FIG. 1 shows a front view of the sonic flosser device.
Figure 2:
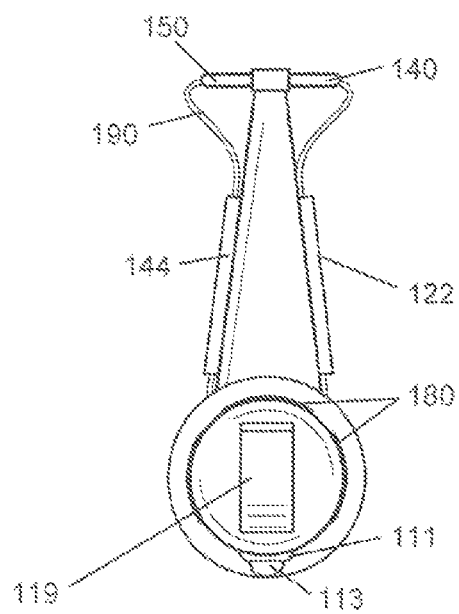
FIG. 2 shows a bottom view of the sonic flosser device.
Figures 3, 4:
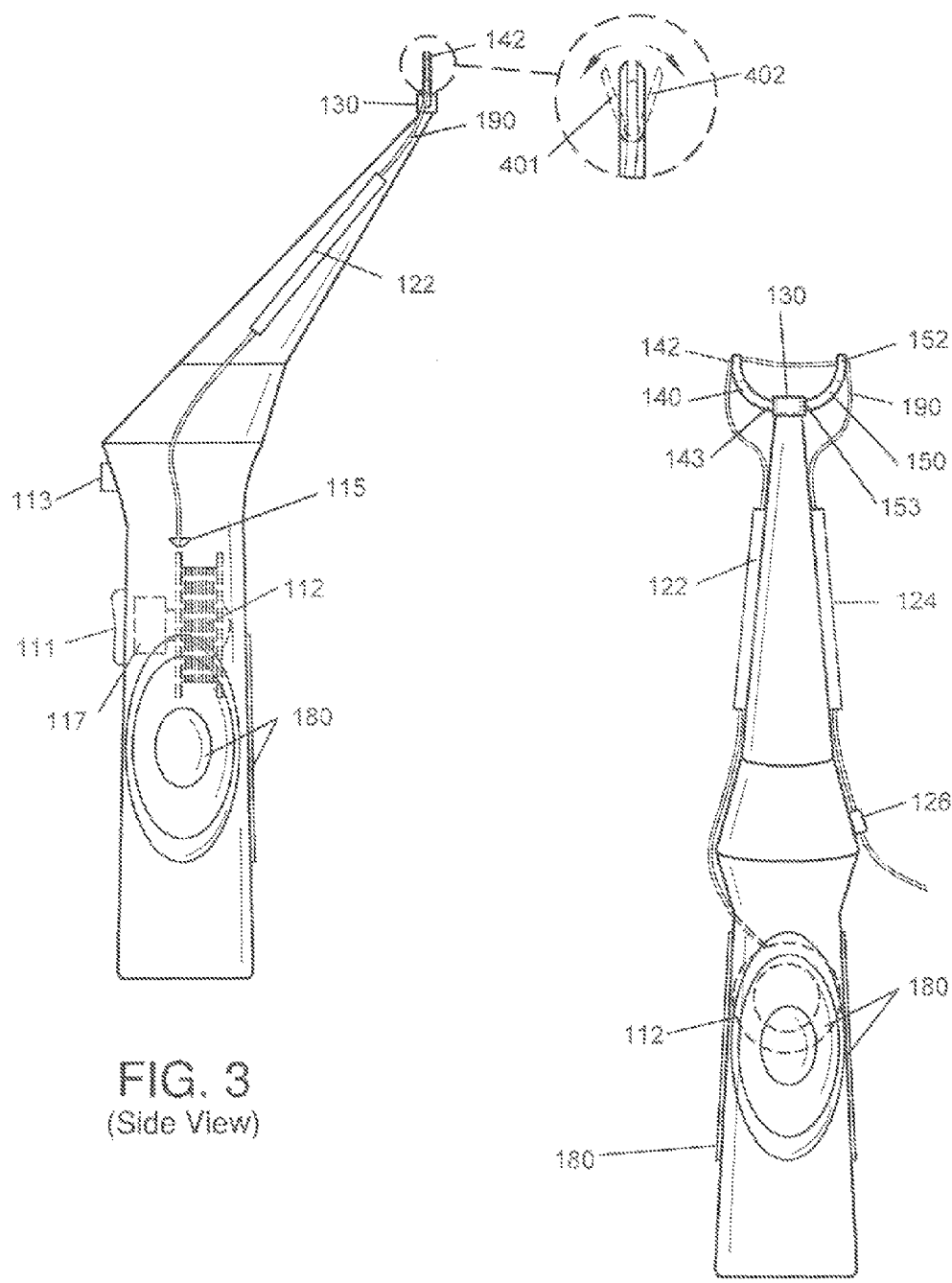
FIG. 3 shows a side view of the sonic flosser device
FIG. 4 shows a back view of the sonic flosser device
Figure 5:
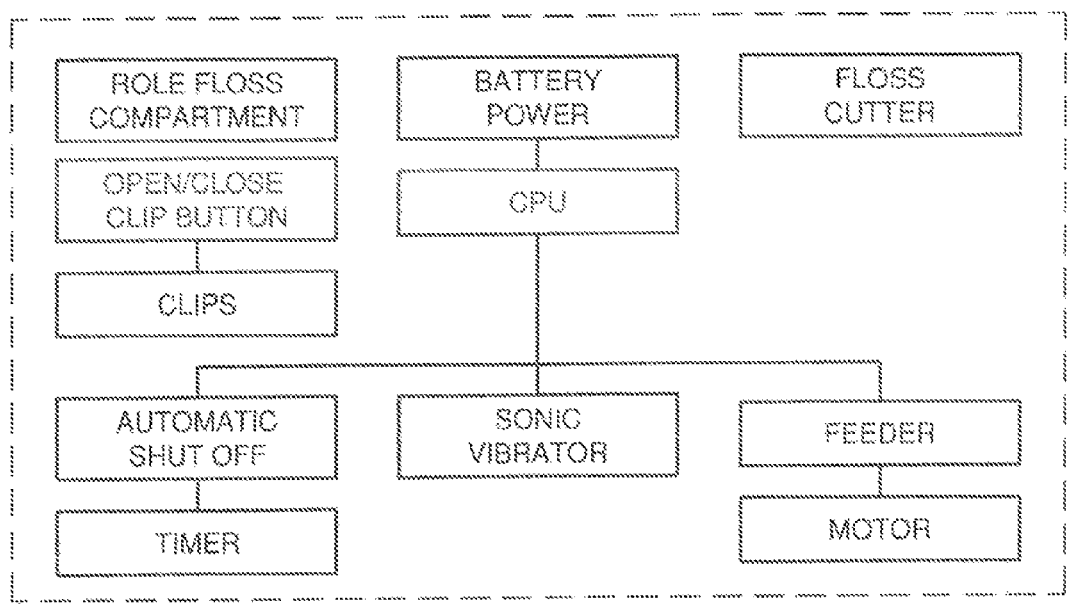
FIG. 5 shows a block diagram of the major components of the flosser device.

Referring now to FIG. 1-5, the present invention features a portable sonic flosser system to assist teeth cleaning. The system 100 comprising a cylindrical handle 110, a hollow extension 120, a vibrator box 130, a first arm 140 disposed along one side of the vibrator, a second arm 150 disposed along the opposite side of the vibrator. The handle has a floss roll 112, a timer 114, a microprocessor 116 and battery 118 disposed inside. A hollow extension with an oblique circular truncated cone shape extends from the handle. The extension has a first elongated hollow rubber guide 122 and second elongated hollow rubber guide 124 disposed on the opposite sides of the circular side surface of the extension and a cutter 126 disposed the circular side surface of the extension.

The cylindrical handle 110 has a first end 210 and second end 320 and a side exterior surface. A power ON/OFF switch 111 and a power indicator light 113 are disposed on the exterior surface. A battery 118 disposed inside the handle with the battery compartment cover 119 located at the second surface, wherein the user can change battery after opening the cover 119. In some embodiments, the battery is one or a plural of regular batteries such as AAA or AA batteries, or rechargeable batteries. In some embodiments, the battery cover 119 is also a charge connector, which is used to re-charge the battery via an external power supply, such as a separate support base with power connection.

In some embodiments, the power indicator light 113 is a LED light. In some embodiments, the brightness of the LED is an indication of the amount of energy remaining in the battery. In some embodiments, the color of the LED is an indication of the amount of energy remaining in the battery. For example, a green color means fully charged battery, a yellow color means that the battery has some energy left but needs recharge soon. A red color means that the battery has almost no energy left and needs recharge as soon as possible.

A hollow extension extends from the first end of the said handle. The extension has an oblique circular truncated cone shape with a base end, top end and a circular side, wherein the base end connects to the first end surface of the said handle and these two ends have the same diameter. The extension has a first elongated hollow rubber guide 122 and second elongated hollow rubber guide 124 disposed on the opposite sides of the circular side surface of the extension and a cutter 126 disposed the circular side surface of the extension.

A vibrator box 130 disposed at the top of the cone extension, wherein the vibrator is operatively connected to the said microprocessor 116 via wires through the interiors of said handle and cone and generates mechanical vibrations at ultrasonic frequencies. In some embodiments, the vibrator is a piezoelectric motor, piezoelectric actuator, piezoelectric vibrator, etc. An ultrasonic vibrator produces much higher stokes per minutes compared to regular motor driven vibrators, thus provides higher efficiency in teeth flossing.

A first arm 140 disposed along one side of the vibrator, a second arm 150 disposed along the opposite side of the vibrator. The arms and the said vibrator form a U shape; wherein the first arm 140 has a distal end 142 and a proximal end 143 with the proximal end connected to the vibrator, the second arm 150 has a distal end 152 and a proximal end 153 with the proximal end connected to the vibrator. The two arms are identical in specification. Each distal end has two flanges 401 and 402 pivotably connected to the distal end. The distance between the flanges is smaller than the diameter of the floss thread such that when the flanged closed, the floss thread can be tightly secured between the flanges. In some embodiments, the flanges are manually opened and closed with the default position as closed. In some embodiments, the flanges are opened and closed via a control button (not shown in the figure) disposed on the exterior surface of the handle. In some embodiments, the flanges are made with material with strong mechanical strength such as metal, reinforced plastics. In some embodiments, the side surface contacting the floss thread are specially treated such as sandblasted to increase the surface friction as a means to further secure the floss thread.

In some embodiments, the arms 140 and 150 are removably connected to the vibrator such that the arms can be removed and cleaned after certain usage.

A thread 190 of floss is extracted from the floss roll 112 inside the handle via the hole 115 and pass through the first rubber guide 122, the first arm 140, the second arm 150, the second rubber guide 124 and the cutter 126, wherein the floss is tightened when flanges (401 and 402) closed; wherein the floss is vibrated together with the arms by the vibrator upon power switch turned on; wherein the floss is further pulled to reload upon power switched turn off and flanges (401 and 402) opened; wherein the used floss is cut at the cutter 126 and trashed.

The microprocessor 116 is operatively connected the said battery 118, timer 114, power switch 111 and vibrator 130. The microprocessor is configured to send vibration signal to the said vibrator upon the power ON/FF switch turned on, stop the vibrator operation upon power ON/FF switch turned off, receive the timer input and stop the vibrator operation upon the preset time runs out. The microprocessor is also configured to monitor the battery information such as battery voltage and send output signal to light up said LED 113 in various levels according to battery information. In some embodiments, the various levels are referred as different brightness of the LED. In some embodiments, the various levels are referred as different colors of the LED. For example, a green color means fully charged battery, a yellow color means that the battery has some energy left but needs recharge soon. A red color means that the battery has almost no energy left and needs recharge as soon as possible.

In some embodiments, a grip pad (180) is disposed on the said handle exterior. The grip pad can be disposed on both sides of the power ON/OFF button. In some embodiments, the grip pad has dots, strips, patterns or a combination thereof on the pad surface.

In some embodiments, a mini-motor (117) is disposed inside the handle to drive the floss roll. The motor is operatively connected to the microprocessor to provide a constant tension of the floss roll.

The disclosures of the following U.S. Patents are incorporated in their entirety by reference herein: U.S. Pat. No. 5,016,660, U.S. Pat. No. 5,069,233, U.S. Pat. No. 5,188,133, U.S. Pat. No. 5,261,430, U.S. Pat. No. 5,264,579, U.S. Pat. No. 5,373,883, U.S. Pat. No. 7,114,506, U.S. Design Pat. No. D493577, U.S. Pat. No. Des. 503,496 and U.S. Pat. No. Des. 526,901.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A portable sonic flosser system to assist teeth cleaning, the system comprising:
   (a) a cylindrical handle (110) comprising a first end (210) and second end (310), wherein the handle comprises an elongated and hollow body, a power ON/OFF switch (111) and a hole (115) disposed on the exterior side surface of the handle (110), a floss roll (112) disposed inside the handle, battery (118) disposed inside the handle, a timer (114) disposed inside the handle and a microprocessor (116) disposed inside the handle;
   (b) a hollow extension (120) extending from the first end (210) of the said handle, wherein the extension has an oblique circular truncated cone shaped with a base end, top end and a circular side, wherein the base end connects to the first end (210) of the said handle (110), wherein the extension (210) has a first elongated hollow rubber guide (122) and second elongated hollow rubber guide (124) disposed on the opposite sides of the circular side surface of the extension and a cutter (126) disposed the circular side surface of the extension;
   (c) a vibrator box (130) disposed at the top of the cone extension, wherein the vibrator is operatively connected to the said microprocessor (116) and generates mechanical vibrations at ultrasonic frequencies;
   (d) a first arm (140) disposed along one side of the vibrator, a second arm (150) disposed along the opposite side of the vibrator, wherein the arms and the said vibrator form a U-shape; wherein the first arm (140) has a distal end (142) and a proximal end (143) with the proximal end connected to the vibrator, wherein the second arm (150) has a distal end (152) and a proximal end (153) with the proximal end connected to the vibrator; wherein each distal end has two flanges (401 and 402) pivotably connected to the distal end;
   wherein the microprocessor (116) is operatively connected the said battery (118), timer (114), power switch (111) and vibrator (130), wherein the microprocessor is configured to send vibration signal to the said vibrator upon the power ON/FF switch turned on, stop the vibrator operation upon power ON/FF switch turned off, receive the timer input and stop the vibrator operation upon the preset time runs out; and
   wherein a thread (190) of floss is extracted from the floss roll (112) inside the handle via the hole (115) and pass through the first rubber guide (122), the first arm (140), the second arm (150), the second rubber guide (124) and the cutter (126), wherein the floss is tightened when flanges (401 and 402) closed; wherein the floss is vibrated together with the arms by the vibrator upon power switch (111) turned on; wherein the floss is further pulled to reload upon power switched turn off and flanges (401 and 402) opened; wherein the used floss is cut at the cutter (126) and trashed.

2. The system of claim 1, wherein the microprocessor is also configured to monitor the battery information such as battery voltage and send output signal to light up said LED (113) in various levels according to battery information.

3. The system of claim 2, wherein the various levels are referred as different brightness of the LED.

4. The system of claim 2, wherein the various levels are referred as different colors of the LED such that a green color means fully charged battery, a yellow color means that the battery has some energy left but needs recharge soon and a red color means that the battery has almost no energy left and needs recharge as soon as possible.

5. The system of claim 1, wherein the vibrator is a piezoelectric motor, piezoelectric actuator or piezoelectric vibrator.

6. The system of claim 1, wherein the battery is one or a plural of batteries.

7. The system of claim 1, wherein the battery is regular battery, or rechargeable battery.

8. The system of claim 1, wherein the cross angle between the said extension and handle is between 120 degree and 180 degree.

9. The system of claim 1, wherein indication light is disposed on the exterior surface of the said handle; wherein the light is on when the power ON/OFF switch is turned ON.

10. The system of claim 1, wherein a grip pad (180) is disposed on the said handle exterior.

11. The system of claim 10, wherein the said grip pad is disposed on both sides of the power ON/OFF button.

12. The system of claim 10, wherein the grip pad has dots, strips, patterns or a combination thereof on the pad surface.

\* \* \* \* \*